(12) United States Patent
Cho et al.

(10) Patent No.: US 8,598,863 B2
(45) Date of Patent: Dec. 3, 2013

(54) APPARATUS AND METHOD FOR DETECTING MOTION CHARACTERISTICS OF PARTICLES IN FLOW CHANNEL

(75) Inventors: Young-Ho Cho, Daejeon (KR); Tae Yoon Kim, Seoul (KR); Dong Woo Lee, Pusan (KR)

(73) Assignee: Korea Advanced Institute of Science and Technology (KAIST), Daejeon (KR)

( * ) Notice: Subject to any disclaimer, the term of this patent is extended or adjusted under 35 U.S.C. 154(b) by 959 days.

(21) Appl. No.: 12/374,092

(22) PCT Filed: Jul. 16, 2007

(86) PCT No.: PCT/KR2007/003442
§ 371 (c)(1),
(2), (4) Date: Jan. 16, 2009

(87) PCT Pub. No.: WO2008/010658
PCT Pub. Date: Jan. 24, 2008

(65) Prior Publication Data
US 2010/0025246 A1    Feb. 4, 2010

(30) Foreign Application Priority Data

Jul. 18, 2006   (KR) .......................... 10-2006-0066825

(51) Int. Cl.
*G01N 27/00*    (2006.01)

(52) U.S. Cl.
USPC ......................... 324/71.4; 204/549; 204/645

(58) Field of Classification Search
None
See application file for complete search history.

(56) References Cited

U.S. PATENT DOCUMENTS 3,927,324 A * 12/1975 Fletcher et al. ............. 250/336.1
6,749,736 B1 * 6/2004 Fuhr et al. .................... 204/643
7,294,249 B2 * 11/2007 Gawad et al. ................. 204/547

* cited by examiner

*Primary Examiner* — Minh N Tang
(74) *Attorney, Agent, or Firm* — Graybeal Jackson LLP; Kevin D. Jablonski (57) ABSTRACT

The present invention is an apparatus and method for detecting the motion characteristics of particles in a flow channel. The apparatus includes first and second electrode groups, each having a pair of electrodes, which are arranged to be spaced apart from each other in a flow channel. The pair of electrodes function as both a drive electrode and a sensing electrode for directly applying voltage and measuring impedance between the electrodes. An operation control unit measures variation in electrical pulses generated in the first and second electrode groups, thus detecting motion characteristics of the particles. The present invention is advantageous in that it does not require complicated optical measuring instruments or analyzing instruments, and in that it can be used to easily detect the motion characteristics of particles in a flow channel merely by analyzing variation in electrical pulses without requiring preliminary information.

26 Claims, 8 Drawing Sheets

Fig. 24 ical signal varies according to the location of the particles, which pass through a region between electrodes forming a pair, relative to the electrodes. This method is advantageous in that, since an electrical measurement method is used, optical equipment is not required, and since the system thereof has a simple structure, the system can be implemented in the microfluidic devices. However, the measurement of the particles is limited to the measurement of a relative location, rather than an absolute location. The magnitude of the electrical signal is also influenced by the size of the particles, variation in the impedance (spectral impedance) of particles according to measurement frequency, and the conductivity of a fluid containing the particles, as well as the location of the particles between electrodes. Accordingly, in order to precisely measure the location of the flow of the particles in the flow channel, preliminary information, such as the size of the particles, spectral impedance of the particles, and the conductivity of the fluid containing the particles, must be known. Further, this method is disadvantageous in that, when the conductivity of the fluid containing the particles is dynamic, when particles have large differences in size and spectral impedance despite being the same type of particles, or when different particles having various sizes and various spectral impedances are mixed together, it is difficult to measure the motion characteristics of the particles.

APPARATUS AND METHOD FOR DETECTING MOTION CHARACTERISTICS OF PARTICLES IN FLOW CHANNEL

TECHNICAL FIELD

The present invention relates, in general, to an apparatus and method for detecting the motion characteristics of particles in a flow channel and, more particularly, to an apparatus and method for detecting the motion characteristics of particles in a flow channel, which make it easy to detect the motion characteristics of particles in a flow channel merely by analyzing electrical signals, without requiring optical measuring instruments or analyzing instruments having complicated structures.

BACKGROUND ART

The detection of the motion characteristics of particles is frequently conducted for characterizing the physical properties of various particles such as metal, polymer, and ceramic particles, and so on. The detection of the motion characteristics of particles in a flow channel is also used as an important means for characterizing biological cells. As an example, many researchers have analyzed the flow of red blood cells, white blood cells, and sperms in microfluidic chips, thus characterizing the oxidative states, chemotaxis properties, and motilities of the biological cells, respectively. [the red blood cell characterization: M. Zborowski, et al., "Red blood cell magnetophoresis, Biophys. J., Vol. 84 (2003) pp. 2638-2645, the white blood cell characterization: D. Irimia, et al., "Microfuidic system for measuring neutrophil migratory responses to fast switches of chemical gradients, Lab. Chip., Vol. 6 (2006) pp. 191-198, and the sperms characterization: B. S. Cho, et al., "Pssively driven integrated microfluidic system for separation of motile sperm, Anal. Chem., Vol. 75 (2003) pp. 1671-1675.]

Further, since the detection of the motion characteristics of particles in a flow channel allows the flow characteristics, such as the flow rate and velocity profile of a fluid, containing particles, in a flow channel, it is a very important technology for measuring a flow rate, diagnosing the internal state of the flow channel, and visualizing flow [flow visualization: D. Sinton, Microscale Flow Visualization, Microfluid Nanofluid, Vol. 1, No. 1 (2004) pp. 2-21.]. In particular, in microfluidic devices, a system, which is sufficiently cheap to be integrated into a single chip and makes it simple to detect the motion characteristics of particles in the flow channel, is urgently required.

Methods of detecting the motion characteristics of particles in a flow channel which are frequently used these days, include particle image velocimetry, fluorescent image tracking velocimetry, laser scattering and dispersion analysis, electrical impedance analysis (particle impedance analysis), etc.

Particle image velocimetry and fluorescent image tracking velocimetry are methods of acquiring the flow image of a typical particle or a fluorescent particle having a fluorescent material attached thereto in a flow channel, analyzing the image, and detecting the motion characteristics of the particle in the flow channel, and are disclosed in U.S. Pat. Nos. 5,124,071 and 5,333,044, respectively. These method are advantageous in that they can analyze the motion of particles having a complicated flow in the flow channel, but are disadvantageous in that, since a microscope, an imaging device and a computer for image data processing are required, high costs are incurred, and since the structure of the system is complicated, it is difficult to implement the microfluidic devices. Further, the method using fluorescent particles is also disadvantageous in that it additionally requires a procedure of attaching fluorescent materials to particles.

The laser scattering and dispersion analysis is a method of radiating laser light onto a flow channel through which particles flow, measuring the degree of optical scattering and dispersion of the laser, appearing when the particles pass through the flow channel, and detecting the motion characteristics of particles in the flow channel, and is disclosed in U.S. Pat. No. 6,867,410. This method does not require a procedure for separately attaching fluorescent materials, but is disadvantageous in that a laser light source, a plurality of optical sensors, and complicated optical instruments are required, so that the system is expensive and has a complicated structure, and thus it is difficult to implement the microfluidic devices. Further, the method has limitations in that particles in a flow channel must have optical characteristics that enable the efficient scattering and dispersion of laser light. Moreover, all of the above optical methods also have limitations in that, since they use optical principles, the material used to make the flow channel must be transparent in order to minimize optical loss.

The particle impedance analysis is a method of measuring the electrical impedance occurring when particles pass through a measurement region of an electrode, and of counting the particles in a flow channel or measuring the size of the particles, the location of the flow of the particles, and the flow rate of the particles, and is disclosed in U.S. Pat. Publication No. 2003-0102854. The method, proposed in U.S. Pat. Publication No. 2003-0102854, is implemented in order to determine the relative location of the flow of the particles in the flow channel on the basis of the fact that the magnitude of the electr

DISCLOSURE

Technical Problem

Accordingly, the present invention has been made keeping in mind the above problems occurring in the prior art, and an object of the present invention is to provide an apparatus and method for detecting the motion characteristics of particles, which do not require complicated optical instruments or analyzing instruments and which can easily detect the motion characteristics of particles, such as the absolute location of the particles in the transverse direction of a flow channel, the speed of the particles in the longitudinal direction of the flow channel, and the traveling direction of the particles, without requiring preliminary information, such as the size of the particles, spectral impedance of the particles, and the conductivity of a fluid containing the particles.

Technical Solution

In accordance with one aspect of the present invention to accomplish the above object, there is provided an apparatus for detecting motion characteristics of particles in a flow channel, comprising first and second electrode groups, each comprising a pair of electrodes, which are arranged to be spaced apart from each other in a flow channel, through which a fluid containing the particles flows, the pair of electrodes functioning as both a drive electrode and a sensing electrode for directly applying voltage and measuring impedance between the electrodes, and an operation control unit for measuring variation in electrical pulses generated in the first and second electrode groups as the particles pass through the flow channel, thus detecting the motion characteristics of the particles.

In accordance with another aspect of the present invention to accomplish the above object, there is provided an apparatus for detecting motion characteristics of particles in a flow channel, comprising a pair of drive electrodes arranged to be spaced apart from each other in the flow channel, through which a fluid containing the particles flows, and adapted to apply a voltage, first and second electrode groups, each comprising a pair of sensing electrodes arranged to be spaced apart from each other between the drive electrodes forming the pair and adapted to measure impedance, and an operation control unit for measuring variation in electrical pulses generated in the first and second electrode groups, as the particles pass through the first and second electrode groups, thus detecting the motion characteristics of particles.

Preferably, the first electrode group may be implemented such that the electrodes forming the electrode pair are arranged so that a distance by which the electrodes are spaced apart from each other is increased in a specific transverse direction of the flow channel, and the second electrode group may be implemented such that the electrodes forming the electrode pair are arranged so that a distance by which the electrodes are spaced apart from each other is decreased in the specific transverse direction of the flow channel.

Preferably, both the pairs of electrodes of the first and second electrode groups may be arranged while being inclined at a certain angle. Further, one of the pair of electrodes of each of the first and second electrode groups may be arranged to be inclined at a certain angle, and a remaining one thereof may be perpendicularly arranged in the transverse direction of the flow channel.

Preferably, the electrodes may be bar-type electrodes, bent electrodes or stepped electrodes.

Preferably, the first and second electrode groups may be arranged on a same surface of the flow channel, or may be arranged, respectively, on any one surface of the flow channel and on an opposite surface of the flow channel. Further, the first and second electrode groups may be arranged on upper/lower surfaces of the flow channel and on left/right surfaces of the flow channel with respect to a flow direction of the particles.

Preferably, the first and second electrode groups may be implemented such that a plurality of electrode groups is additionally arranged in series or in parallel.

Preferably, each of the first and second electrode groups may comprise a plurality of electrodes, and the electrode pair may be implemented by selecting electrodes from among the plurality of electrodes and by combining them with each other. Preferably, each of the first and second electrode groups may comprise electrodes forming the electrode pair. Preferably, the electrode pairs of the first and second electrode groups may be implemented using a single common electrode.

In accordance with a further aspect of the present invention to accomplish the above object, there is provided method of detecting motion characteristics of particles in a flow channel, comprising a first step of directly applying voltage to first and second electrode groups, each comprising a pair of electrodes, which are arranged to be spaced apart from each other in a flow channel, through which a fluid containing the particles flows, the pair of electrodes functioning as both a drive electrode and a sensing electrode, thus generating respective electric fields in the flow channel, a second step of moving the particles placed in the flow channel, thus causing the particles to vary electrical pulses while the particles pass through electrical fields generated in the first and second electrode groups, and a third step of an operation control unit detecting motion characteristics of particles, such as location of the particles in a transverse direction of the flow channel, a speed of the particles in a longitudinal direction of the flow channel, and a traveling direction of the particles on the basis of variation in electrical pulses measured in the first and second electrode groups.

In accordance with yet another aspect of the present invention to accomplish the above object, there is provided a method of detecting motion characteristics of particles in a flow channel, comprising a first step of applying voltage to a pair of drive electrodes arranged to be spaced apart from each other in a flow channel, through which a fluid containing the particles flows, thus generating electric fields in the flow channel, a second step of moving the particles in the flow channel, thus causing the particles to vary electrical pulses while the particles pass through the electrical fields generated in first and second electrical groups, each comprising a pair of sensing electrodes arranged to be spaced apart from each other between the drive electrodes forming the pair, and a third step of an operation control unit detecting motion characteristics of the particles, such as location of the particles in a transverse direction of the flow channel, a speed of the particles in a longitudinal direction of the flow channel, and a traveling direction of the particles, on a basis of variation in the electrical pulses measured in the first and second electrode groups.

Preferably, at the third step, the operation control unit may detect the location of the particles in the transverse direction of the flow channel on a basis of a ratio of durations of electrical pulses measured in the first and second electrode groups.

Preferably, at the third step, the operation control unit may detect the traveling direction of the particles in the flow channel in the longitudinal direction of the flow channel on a basis of a sequence of generation of the electrical pulses respectively measured in the first and second electrode groups.

Preferably, at the third step, the operation control unit may detect the speed of the particles in the flow channel in the longitudinal direction of the flow channel on a basis of a sum of durations of the electrical pulses respectively measured in the first and second electrode groups, and a sum of a distance of the first electrode groups in the longitudinal direction of the flow channel and a distance of the second electrode groups in the longitudinal direction of the flow channel.

Advantageous Effects

As described above, the present invention provides an apparatus and method for detecting the motion characteristics of particles in a flow channel, which are advantageous in that they can easily detect the motion characteristics of particles, such as the location of the particles in the transverse direction of a flow channel, the speed of the particles in the longitudinal direction of the flow channel, and the traveling direction of the particles, on the basis of variation in electrical pulses measured in a plurality of electrodes, which are inclined at an arbitrary angle and disposed along the longitudinal direction of the flow channel.

Further, the present invention is advantageous in that it does not require an optical instrument or an analyzing instrument having high manufacturing costs and complicated structures, and in that it can be used to easily detect the motion characteristics of particles without requiring preliminary information, such as the size of particles, the spectral impedance of the particles for the measurement frequency, and the conductivity of the fluid containing the particles.

DESCRIPTION OF DRAWINGS

The above and other objects, features and other advantages of the present invention will be more clearly understood from the following detailed description taken in conjunction with the accompanying drawings, in which.

BEST MODE

Reference should now be made to the drawings, in which the same reference numerals are used throughout the different drawings to designate the same or similar components.

The present invention proposes technology for detecting the motion characteristics of particles in a flow channel through particle impedance analysis without requiring any optical instrument, and the principles thereof are primarily described.

Figure 1:
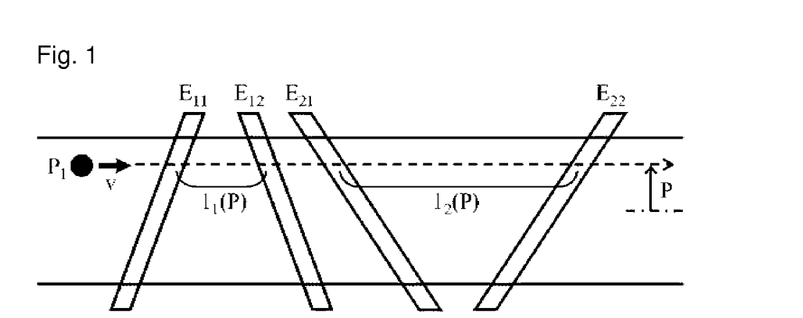
FIGS. 1 and 2 are diagrams schematically showing the principles of the detection of the motion characteristics of particles in a flow channel according to the present invention.
Figure 2:
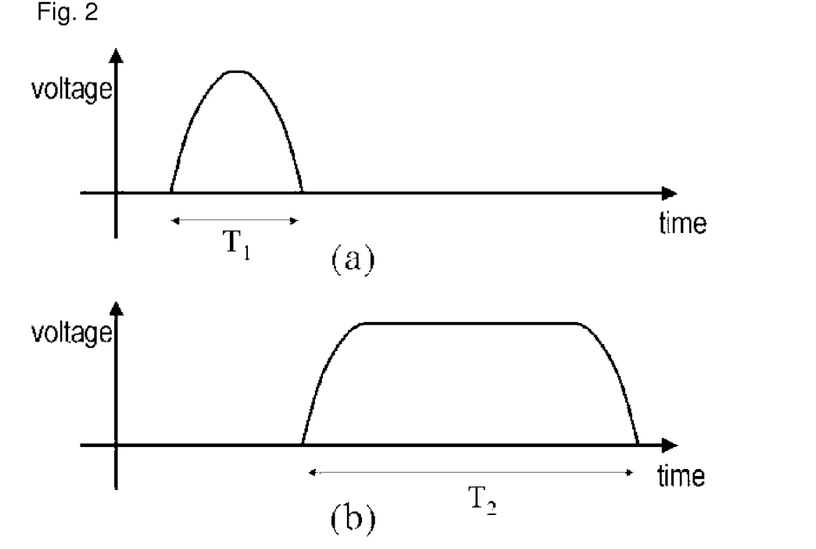

FIGS. 1 and 2 are diagrams schematically showing the principles of the detection of the motion characteristics of particles in a flow channel according to the present invention.

As shown in FIG. 1, in order to describe the principles of the present invention, the following conditions must be satisfied as preconditions. That is, first, a particle $P_1$ must pass through electrodes $E_{11}$ to $E_{22}$ in the direction parallel to a flow channel. Second, each particle must sequentially pass through the region between the electrodes $E_{11}$ and $E_{12}$ and the region between the electrodes $E_{21}$ and $E_{22}$. Third, the particle must pass through the electrodes at a uniform velocity (v).

Under such preconditions, a first electrical pulse is generated while the particle passes through the region between the electrodes $E_{11}$ and $E_{12}$ of a first electrode group, and a second electrical pulse is generated while the particle passes through the region between the electrodes $E_{21}$ and $E_{22}$ of a second electrode group. Consequently, two signals, as shown in FIG. 2, are obtained.

Next, the principles of the measurement of the location where the particle passes, among the motion characteristics of the particle in the flow channel, are described. The ratio of the first duration $T_1$ of the first electrical pulse and the duration $T_2$ of the second electrical pulse can be represented as a function of the location P of the particle, as shown in Equation [1], under the condition that the particle travels at a uniform velocity. That is, the ratio R of durations is measured, and thus the passing location P of the particle can be obtained, $$R = \frac{T_2}{T_1 + T_2} + \frac{\{l_2(P)\}/v}{\{l_1(p) + l_2(P)\}/v} = \frac{l_2(P)}{l_1(P) + l_2(P)} \quad [1]$$

where $l_1(P)$ and $l_2(P)$ are distances between the electrodes of the first electrode group and between the electrodes of the second electrode group, respectively, which correspond to the travel path of the particle. The distances $l_1(P)$ and $l_2(P)$ are determined by the passing location P of the particle.

Further, the principles of the measurement of the velocity at which the particle passes through a flow channel, among the motion characteristics of the particle in the flow channel, are described. The sum T of the duration $T_1$ of the first electrical pulse and the duration $T_2$ of the second electrical pulse is represented using the following Equation [2].

$$T = T_1 + T_2 = \{l_1(P) + l_2(P)\}/v \quad [2]$$

However, the passing location P of the particle can be obtained from Equation [1], and $l_1(P)$ and $l_2(P)$ are known designed values, and the sum T of the durations is measured, thus obtaining the velocity v at which the particle passes through the flow channel.

For example, when the angles of the slopes of the electrodes, constituting the first and second electrode groups, are identical to each other, the duration ratio R and the particle location P have the relationship of a linear equation, as shown in Equation [3], which will be described later.

However, when the angles of the slopes of the electrodes, constituting the first and second electrode groups, are different from each other, as shown in FIG. 1, the duration ratio R and the particle location P have a non-linear relationship, as shown in Equation [1].

Further, the present invention can use two well-known methods to measure the particle using electrodes. That is, as disclosed in U.S. Pat. No. 6,169,394, voltage is directly applied to sensing electrodes, and the impedance between the sensing electrodes is measured, and thus the size and impedance of the particle can be measured. Further, as disclosed in U.S. Pat. Publication No. 2003-0102854, after a sensing electrode and a drive electrode are respectively implemented, voltage is applied to the drive electrode, and the impedance between the sensing electrodes is measured using the sensing electrode, thus measuring the size and impedance of the particle.

As described above, since the apparatus and method for detecting the motion characteristics of particles in a flow channel according to the present invention introduces an electrical method, complicated optical instruments and analyzing instruments are not required. Further, since the apparatus and method for detecting the motion characteristics of particles in a flow channel according to the present invention are based on the duration of electrical signals, which are not influenced by the size of particles, spectral impedance of particles, the conductivity of a fluid containing the particles, etc., the motion characteristics of particles can be detected without requiring related preliminary information. Moreover, since the duration characteristics of electrical signals vary across the entire measurement range, the absolute location of particles in the transverse direction of the flow channel can be measured.

Hereinafter, a preferred embodiment of an apparatus for detecting the motion characteristics of particles in a flow channel according to the present invention will be described with reference to the attached drawings.

Figure 3:
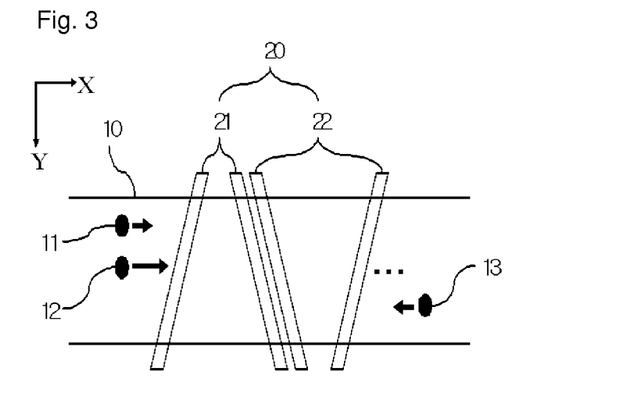
FIG. 3 is a diagram schematically showing electrodes used in an apparatus for detecting the motion characteristics of particles in a flow channel according to an embodiment of the present invention.

FIG. 3 is a diagram schematically showing electrodes used in the apparatus for detecting the motion characteristics of particles in a flow channel according to an embodiment of the present invention.

As shown in FIG. 3, the apparatus for detecting the motion characteristics of particles in a flow channel according to the embodiment of the present invention detects the motion characteristics of particles 11, 12, and 13 in a flow channel 10 through particle impedance analysis without requiring an optical instrument. In particular, the apparatus has the following construction so that the motion characteristics of the particles 11, 12, and 13 can be easily detected without using preliminary information, such as the size of the particles 11, 12, and 13, the spectral impedance of the particles 11, 12, and 13, or the conductivity of the fluid in the flow channel.

That is, the apparatus for detecting the motion characteristics of particles in a flow channel according to the embodiment of the present invention includes electrodes 20 for generating electric fields in the flow channel 10 so as to detect the motion characteristics of the particles 11, 12, and 13, which move in the flow channel 10, and an operation control unit for measuring variation in electrical pulses generated in the electrodes 20 when the particles 11, 12, and 13 pass through the electrodes 20, and for detecting the motion characteristics of the particles 11, 12, and 13.

The electrodes 20 according to this embodiment are implemented so that a plurality of electrodes is sequentially arranged in the longitudinal direction X of the flow channel 10, and, preferably, bar-type electrodes 20 are used as the electrodes. Further, among the plurality of electrodes 20, electrodes forming a pair have shapes that are inclined at a certain angle so that the distance by which the electrodes are spaced apart from each other is increased in a specific transverse direction Y of the flow channel 10. In this case, the electrodes forming the pair are designated as a first electrode group 21. Among the plurality of electrodes, other electrodes forming another pair are placed to allow the particles 11 and 12, having passed through the first electrode group 21, to subsequently pass therethrough, and have shapes inclined at the same angle as the first electrode group 21 so that the distance by which the electrodes are spaced apart from each other is decreased in the specific transverse direction Y of the flow channel 10. In this case, the electrodes forming the pair are designated as a second electrode group 22. In this case, even if the determination is conducted on the basis of the particle 13, traveling in a direction different from those of the particles 11 and 12 in the flow channel 10, the first and second electrode groups 21 and 22 are defined using the same method as the above method.

Figure 4:
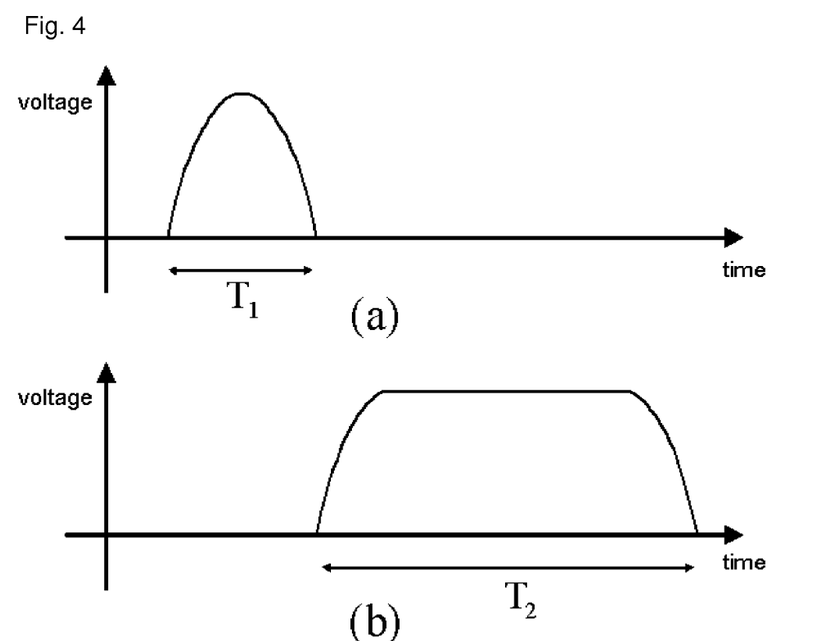
FIGS. 4 to 6 are graphs showing variation in electrical pulses according to the motion characteristics of particles passing through the electrode groups of FIG. 3.
Figure 5:
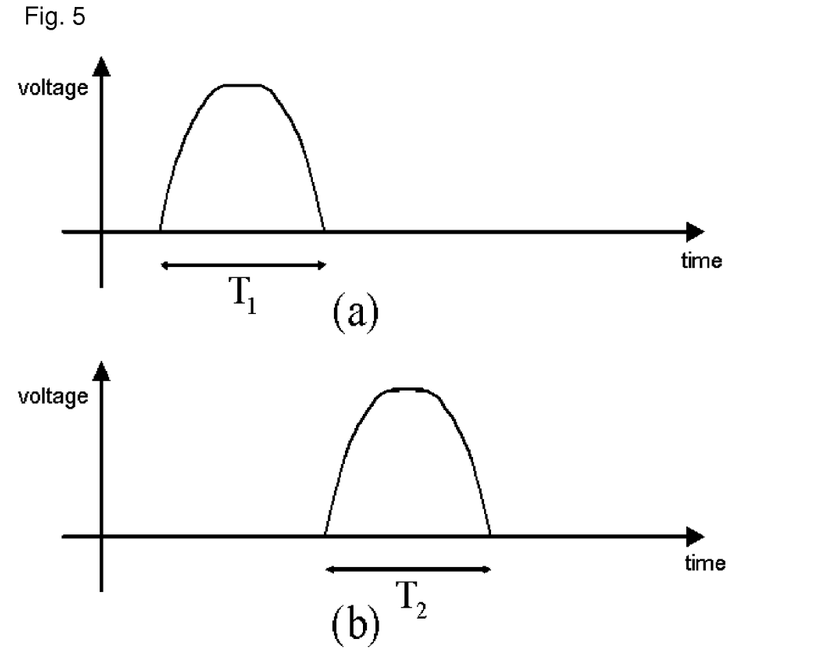
Figure 6:
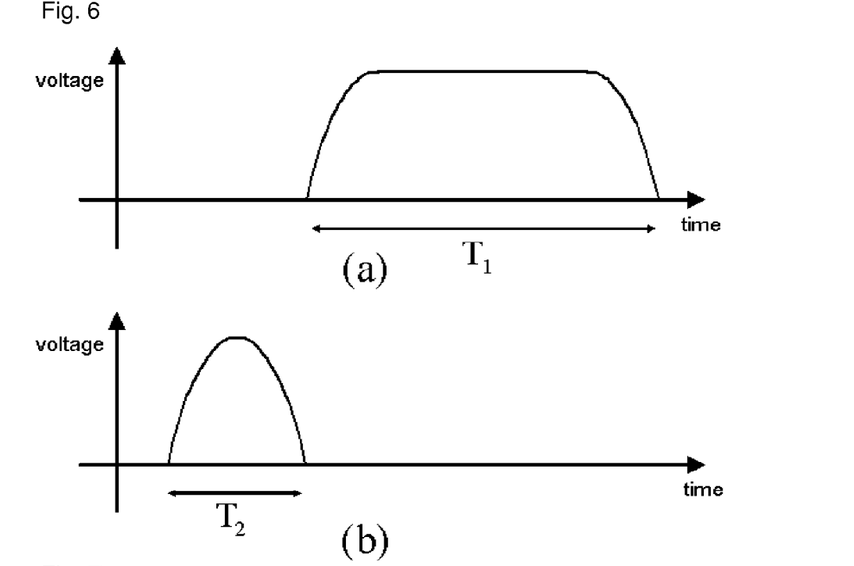

FIG. 4 illustrates graphs showing the electrical pulses measured in the first and second electrode groups 21 and 22 while the first particle 11 of FIG. 3 moves in the flow channel 10. FIG. 5 illustrates graphs showing the electrical pulses measured in the first and second electrode groups 21 and 22 while the second particle 12 of FIG. 3 moves in the flow channel 10. FIG. 6 illustrates graphs showing the electrical pulses measured in the first and second electrode groups 21 and 22 while the third particle 13 of FIG. 3 moves in the flow channel 10.

In this embodiment, the motion characteristics of the particles 11, 12, and 13 can be easily detected using the results of the graphs showing variation in the electrical pulses of FIGS. 4 to 6.

First, the location in the transverse direction Y of the flow channel at which each of the particles 11, 12, and 13 passes through the first and second electrode groups 21 and 22 can be detected on the basis of the ratio of the times required for each of the particles 11, 12, and 13 to pass through the first and second electrode groups 21 and 22, that is, the ratio of the durations $T_1$ and $T_2$ of the electrical pulses ($R=T_2/(T_1+T_2)$). The locations of the particles 11, 12 and 13 in the transverse direction of the flow channel 10 can be calculated using the following Equation [3].

$$R = \frac{T_2}{T_1 + T_2} = \left(\frac{l_2 - l_4}{wL}\right) \cdot P + \left(\frac{l_2 + l_4}{2L}\right) \quad [3]$$

In Equation [3], R is the ratio of the duration of the electrical pulse generated in the second electrode group to the sum of the durations of the electrical pulses generated in the first and second electrode groups, $T_1$ is the duration of the electrical pulse generated while a particle passes through the first electrode group 21, $T_2$ is the duration of the electrical pulse generated while the particle passes through the second electrode group 22, $l_2$ and $l_4$ are the maximum and minimum distances between the electrodes of the second electrode group 22, L is the total distance between the first and second electrode groups 21 and 22, w is the width of the flow channel 10, and P is the location of the particle in the transverse direction of the flow channel 10 when the center line of the flow channel 10 is set to a reference.

In Equation [3], $l_2$, $l_4$, w, and L are values that can be determined when the electrodes 20 are installed in the flow channel 10. Therefore, if the value of the duration ratio R of the electrical pulses is determined, the location P of the particle in the transverse direction of the flow channel 10 can be calculated.

Second, the speed in the longitudinal direction X of the flow channel, at which each of the particles 11, 12, and 13 passes through the first and second electrode groups 21 and 22, can be detected on the basis of the sum $T=T_1+T_2$ of the durations for which each of the particles 11, 12, and 13 passes through the first and second electrode groups 21 and 22. That is, since the equation for speed is distance/time (m/s), as is well known to those skilled in the art, the speed of each of the particles 11, 12, and 13 can be calculated using both a sum of a distance $l_1(P)$ of the first electrode groups 21 in the longitudinal direction of the flow channel and a distance $l_2(P)$ of the second electrode groups 22 in the longitudinal direction of the flow channel and the time it takes for the particle to pass through the first and second electrode groups 21 and 22, that is, the sum T of the durations of the electrical pulses.

Third, the traveling direction in the longitudinal direction X of the flow channel, in which each of the particles 11, 12, and 13 passes through the first and second electrode groups 21 and 22, can be detected on the basis of the sequence of the generation of measured electrical pulses.

Respective views (a) of FIGS. 4 to 6 illustrate the electrical pulses measured in the first electrode group 21, and respective views (b) of FIGS. 4 to 6 illustrate the electrical pulses measured in the second electrode group 22. It can be seen that the ratio $R=T_2/(T_1+T_2)$ of the durations of electrical pulses of FIGS. 4 to 6 also varies according to different locations at which each of the particles 11, 12, and 13 passes through the first and second electrode groups. Further, it can be seen that the sum $T=T_1+T_2$ of the durations of the electrical pulses of FIGS. 4 and 6 and the sum $T=T_1+T_2$ of the durations of the electrical pulses of FIG. 5 also vary according to the different speeds at which each of the particles 11, 13 and 12 passes through the first and second electrode groups 21 and 22. Finally, it can be seen that the sequence of generation of the electrical pulses of FIGS. 4 and 5 and the sequence of generation of the electrical pulses of FIG. 6 also vary according to different directions, in which each of the particles 11, 12, and 13 passes through the first and second electrode groups 21 and 22. Consequently, the location, speed, and traveling direction of particles can be simultaneously detected using the variation in electrical pulses on the basis of the above-described principles of the present invention.

Figure 7:
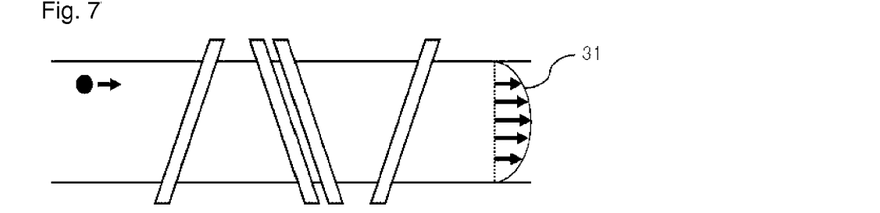
FIGS. 7 and 8 are diagrams schematically showing speed distribution and fluid flow of particles passing through the electrodes groups of FIG. 3.
Figure 8:
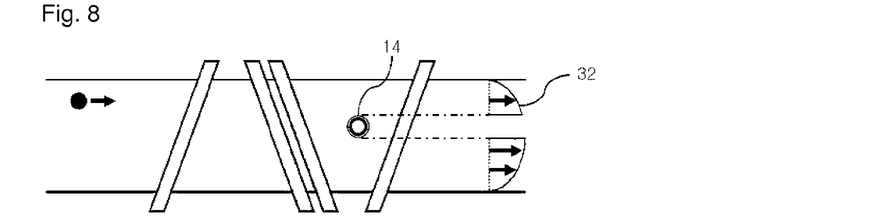

FIGS. 7 and 8 are diagrams schematically showing speed distribution and fluid flow of particles passing through the electrodes groups of FIG. 3. The apparatus for detecting motion characteristics of particles in the flow channel according to the present invention can detect speed distribution and aspect 31 of fluid flow of particles as illustrated in FIG. 7 based on the location, speed, and traveling direction of particles. Also, as illustrated in FIG. 8, speed distribution and aspect 32 of fluid flow of particles to be measured when the particles 14 is attached to the wall of the flow channel comprise a space at a point corresponding to location attached to the flow channel. Therefore, plugging in the flow channel du to particles can be sensed by inspecting speed distribution changes of particles detected by the apparatus for detecting motion characteristics of particles in a flow channel according to the present invention.

Figure 9:
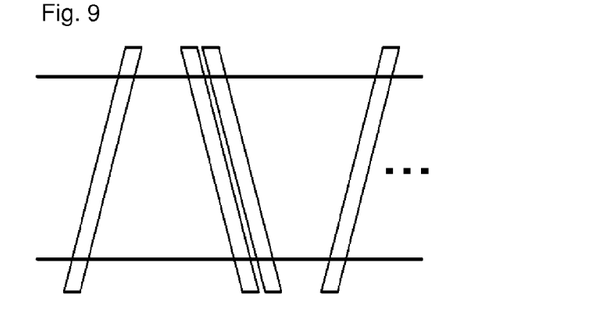
FIGS. 9 to 12 are diagrams schematically showing various shapes of the electrodes of FIG. 3.
Figure 10:
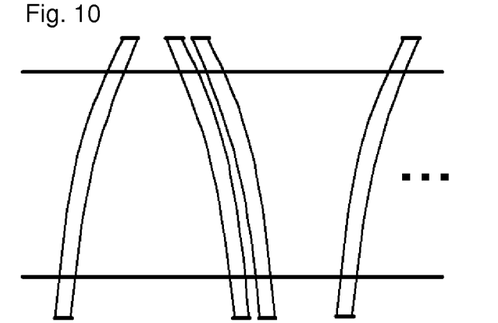
Figure 11:
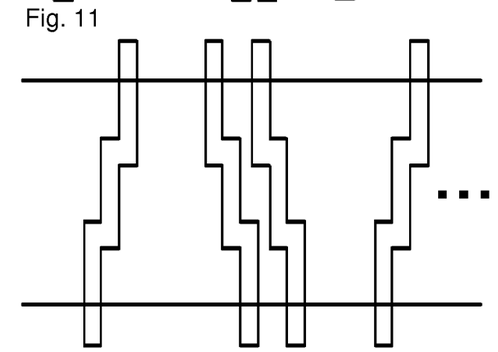
Figure 12:
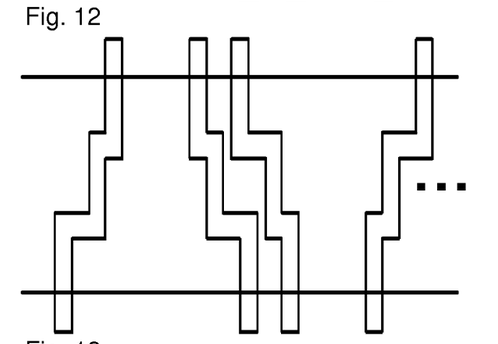

FIGS. 9 to 12 are diagrams schematically showing various shapes of the electrodes of FIG. 3. FIGS. 9 and 10 illustrate successive electrodes, and show the cases where bar-type electrodes and bent electrodes are respectively used. FIGS. 11 and 12 show that stepped electrodes can also be used.

Figure 13:
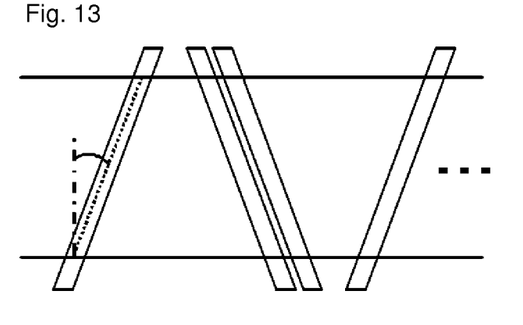
FIGS. 13 to 15 are diagrams schematically showing the cases where the slope of a pair of electrodes of FIG. 3, the width of the flow channel, and the distance between electrodes, respectively, are differently set.
Figure 14:
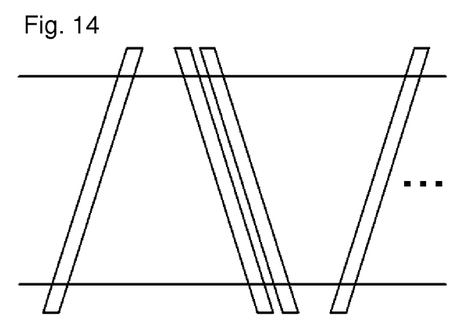
Figure 15:
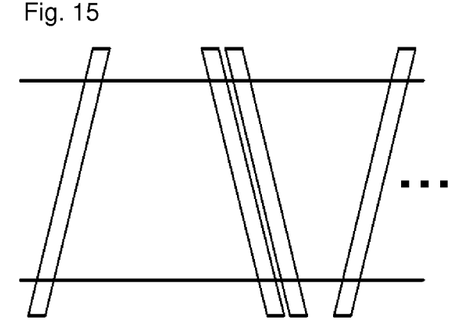

FIGS. 13 to 15 are diagrams schematically showing the cases where the slope of the pair of electrodes of FIG. 3, the width of the flow channel, and the distance between the electrodes is differently set, and show that it does not matter if the slope of the pair of electrodes, the width of the flow channel, or the distance between the electrodes is variously changed during a procedure for installing the electrodes 20 in the flow channel 10.

Figure 16:
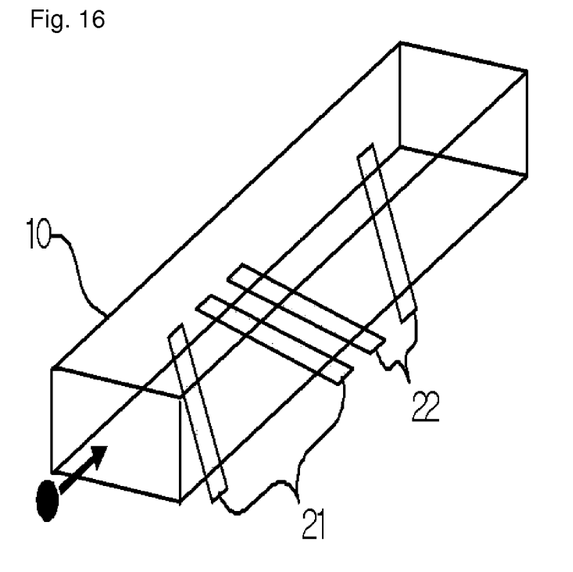
FIGS. 16 to 20 are diagrams schematically showing states in which the electrodes of FIG. 3 are arranged in the flow channel.
Figure 17:
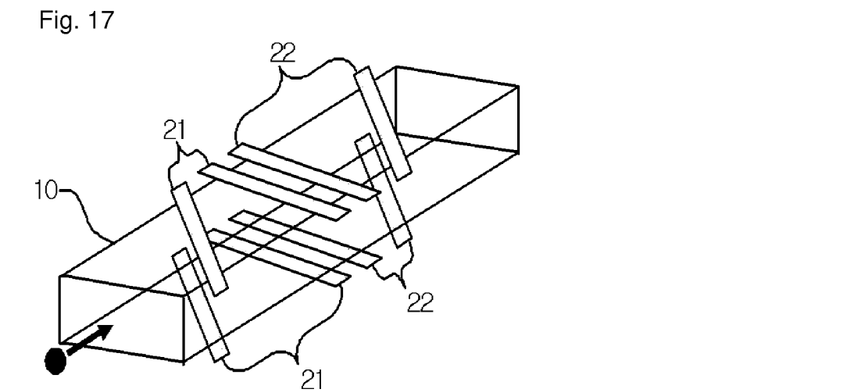
Figure 18:
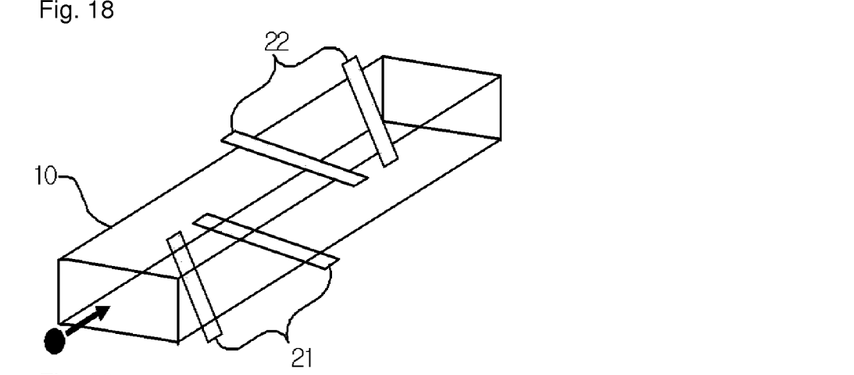
Figure 19:
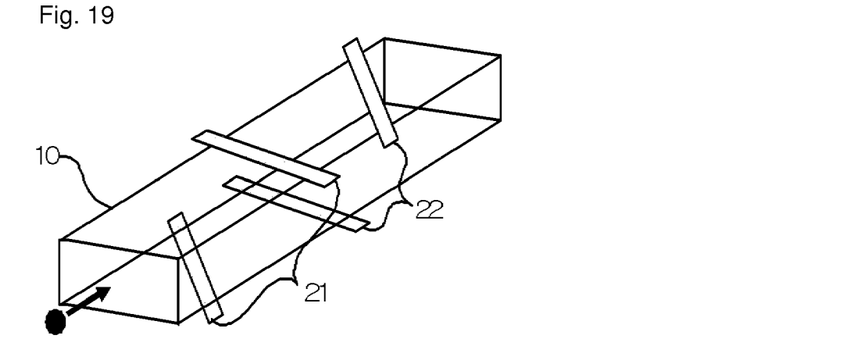

FIGS. 16 to 20 are diagrams schematically showing the states in which the electrodes of FIG. 3 are arranged in a flow channel. That is, as shown in FIG. 16, the electrodes of the first electrode group 21 and the second electrode group 22 are arranged on the same surface of the flow channel 10. Further, as shown in FIG. 17, the electrodes of the first and second electrode groups 21 and 22 can be arranged together on the upper and lower surfaces of the flow channel 10. Further, as shown in FIG. 18, the electrodes of the first electrode group 21 can be arranged on any one surface of the flow channel 10, and the electrodes of the second electrode group 22 can be arranged on the opposite surface of the flow channel 10. Further, as shown in FIG. 19, one of the electrodes constituting each of the first and second electrode groups 21 and 22 may be arranged on any one surface of the flow channel 10, and the other thereof may be arranged on the opposite surface of the flow channel 10. In FIGS. 16 to 19, electrodes are arranged on the upper and lower surfaces of the flow channel on the basis of the traveling direction of the particles, but may be arranged on left and right surfaces of the flow channel, using the same method as the above method.

Figure 20:
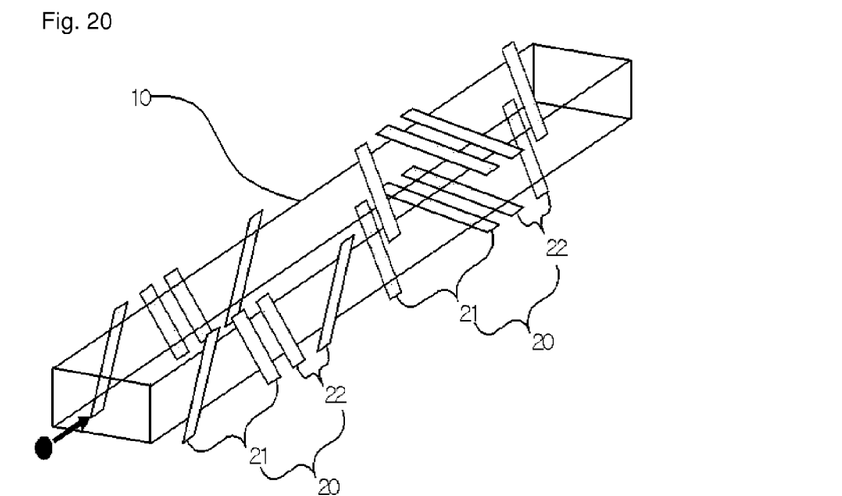

Further, as shown in FIG. 20, the electrodes 20 can be arranged such that the electrodes of the first and second electrode groups 21 and 22 are arranged on the upper/lower surfaces and left/right surfaces of the flow channel 10. When the electrodes are arranged on the upper/lower and left/right surfaces of the flow channel in this way, the location, speed and traveling direction of particles in the horizontal direction of the flow channel and the location, speed and traveling direction of the particles in the vertical direction of the flow channel can be measured together, and thus the motion characteristics of the particles for the section of the flow channel can be effectively observed.

Figure 21:
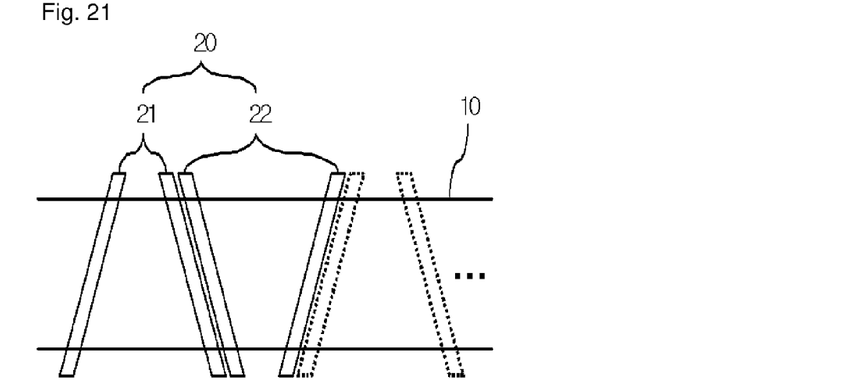
FIGS. 21 and 22 are diagrams schematically showing embodiments in which some effective electrodes can be selected from among a plurality of electrode groups of FIG. 3 and can be used.
Figure 22:
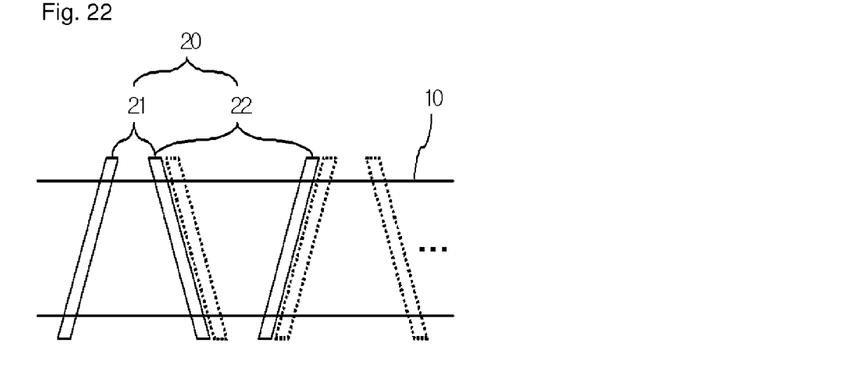

FIGS. 21 and 22 are diagrams schematically showing an embodiment in which some effective electrodes can be selected from among a plurality of electrode groups of FIG. 3, and can be used. That is, this embodiment can be implemented so that a plurality of electrodes 20 is arranged along the longitudinal direction of the flow channel 10, an effective pair of electrodes can be selected from among the electrodes 20 and can be used as the first electrode group 21, and another effective pair of electrodes can be selected from among the electrodes 20 and can be used as the second electrode group 22. In this case, as shown in FIG. 20, a single electrode can be used as a common electrode for the first and second electrode groups 21 and 22. As described above, a method of using a single electrode as a common electrode and consequently using three electrodes can be implemented such that, as shown in FIG. 22, effective electrodes, forming an electrode pair, can be selected from among the plurality of electrodes, and, alternatively, the first and second electrode groups 21 and 22 can be implemented using only three electrodes.

Figure 23:
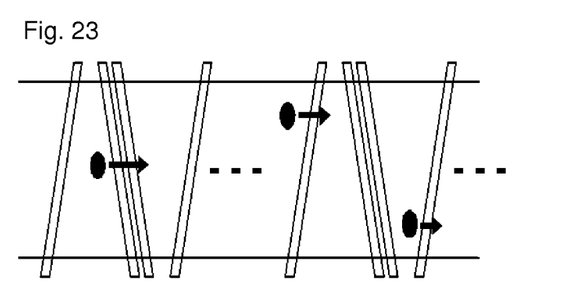
FIGS. 23 and 24 are diagrams schematically showing states in which the plurality of electrode groups of FIG. 3 is arranged in series and in parallel, respectively.
Figure 24:
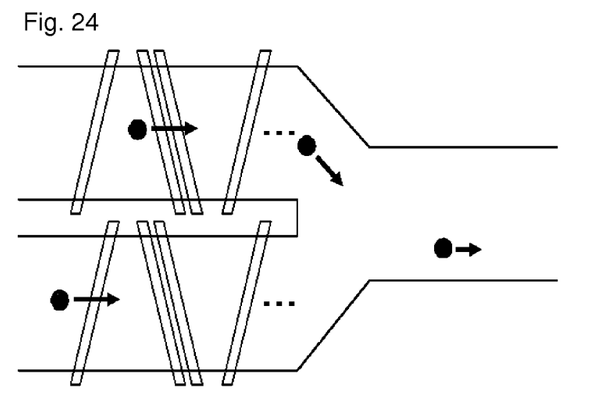

FIGS. 23 and 24 are diagrams schematically showing the states in which the electrode groups of FIG. 3 are arranged in series or in parallel. In the present invention, a plurality of electrode groups can be arranged in series or in parallel.

Hereinafter, a preferred embodiment of a method of detecting the motion characteristics of particles in a flow channel according to the present invention is described below.

First, in this embodiment, a first electrode group 21 is composed of a pair of electrodes, which are inclined at a certain angle so that the distance by which the electrodes of the first electrode group 21 are spaced apart from each other is increased in a specific transverse direction of the flow channel 10. A second electrode group 22 is composed of a pair of electrodes, which are arranged in the longitudinal direction of the flow channel 10 to allow the particles, having passed through the first electrode group 21, to pass through the second electrode group 22, and which are inclined at the same angle as the first electrode group 21 so that the distance by which the electrodes of the second electrode group 22 are spaced apart from each other, is decreased in the specific transverse direction of the flow channel 10. The first and second electrode groups 21 and 22 generate respective electric fields in the flow channel 10.

Next, in this embodiment, particles placed in the flow channel 10 are moved using inner and outer driving forces, so that the particles vary electrical pulses while passing through the electric fields generated in the first and second electrode groups 21 and 22.

Finally, on the basis of the variation in electrical pulses measured in the first and second electrode groups 21 and 22, the operation control unit detects the motion characteristics of the particles, such as the location of the particles in the transverse direction of the flow channel 10, the speed of the particles in the longitudinal direction of the flow channel 10, and the traveling direction of the particles.

However, in the last stage of the embodiment, the operation control unit detects the location of the particles in the transverse direction of the flow channel 10 on the basis of the ratio R of the durations of the electrical pulses respectively measured in the first and second electrode groups 21 and 22. Further, in the last stage of this embodiment, the operation control unit detects the traveling direction of the particles in the flow channel 10 in the longitudinal direction of the flow channel 10 on the basis of the sequence of the generation of the electrical pulses respectively measured in the first and second electrode groups 21 and 22. Further, in the last stage of this embodiment, the operation control unit detects the speed of the particles in the longitudinal direction of the flow channel 10 on the basis of the sum T of the durations of the electrical pulses respectively measured in the first and second electrode groups 21 and 22.

In the above embodiments, the case where the angles of the slopes of the electrodes of the first electrode group and the second electrode group are identical to each other is described as an example. However, the present invention can be implemented such that the angles of the slopes of the electrodes of the first and second electrode groups are differently set, as shown in FIG. 1. Further, in the present invention, any one of the electrodes constituting each of the first and second electrode groups can be perpendicularly arranged in the transverse direction of the flow channel, without all of the electrodes constituting the first and second electrode groups being arranged to be inclined.

Further, in the above-described embodiments, all of the electrodes constituting the first and second electrode groups are constructed to function as both a drive electrode and a sensing electrode for directly applying voltage and measuring impedance between the electrodes, as in the case of U.S. Pat. No. 6,169,394. However, the present invention can be implemented such that, as in the case of U.S. Pat. Publication No. 2003-0102854, a pair of drive electrodes for applying voltage is separately installed, and electrodes disposed between the drive electrodes to constitute the first and second electrode groups, function only as sensing electrodes for measuring the impedance between the electrodes.

INDUSTRIAL APPLICABILITY

As described above, the present invention provides an apparatus and method for detecting the motion characteristics of particles in a flow channel, which are advantageous in that they can easily detect the motion characteristics of particles, such as the location of the particles in the transverse direction of a flow channel, the speed of the particles in the longitudinal direction of the flow channel, and the traveling direction of the particles, on the basis of variation in electrical pulses measured in a plurality of electrodes, which are inclined at an arbitrary angle and disposed along the longitudinal direction of the flow channel.

Further, the present invention is advantageous in that it does not require an optical instrument or an analyzing instrument having high manufacturing costs and complicated structures, and in that it can be used to easily detect the motion characteristics of particles without requiring preliminary information, such as the size of particles, the spectral impedance of the particles for the measurement frequency, and the conductivity of the fluid containing the particles.

Although the preferred embodiments of an apparatus and method for detecting the motion characteristics of particles according to the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for detecting motion characteristics of particles in a flow channel through which a fluid containing the particles flows, comprising:
    first and second electrode groups, each electrode group comprising a pair of electrodes functioning as both a drive electrode and a sensing electrode for directly applying voltage and measuring impedance between the pair of electrodes; and,
    an operation control unit for measuring variation in electrical pulses generated in the first and second electrode groups as the particles pass through the flow channel, thus detecting the motion characteristics of the particles,
    wherein the first electrode group and the second electrode group are sequentially arranged in a longitudinal direction X of the flow channel with both of the first and second electrode groups being positioned on the same surface plane of the flow channel, one electrode of the first electrode group is inclined at a first angle to the other electrode so that a distance $l_1(P)$ by which the electrodes of the first electrode group are spaced apart from each other in the longitudinal direction is increased in a specific transverse direction Y of the flow channel, while one electrode of the second group is inclined at a second angle to the other electrode so that a distance $l_2(P)$ by which the electrodes of the second group are spaced apart from each other in the longitudinal direction is decreased in the specific transverse direction of the flow channel.

2. The apparatus according to claim 1, wherein the first angle is identical to the second angle.

3. The apparatus according to claim 1, wherein the first and second angles are selected such that one of the pair of electrodes of each of the first and second electrode groups is arranged to be inclined at a certain angle to the transverse direction, and a remaining one thereof is arranged in the transverse direction of the flow channel.

4. The apparatus according to claim 1, wherein the electrodes are bar-type electrodes, bent electrodes or stepped electrodes.

5. The apparatus according to claim 1, wherein the first and second electrode groups are arranged on upper/lower surfaces of the flow channel with respect to the flow direction.

6. The apparatus according to claim 1, wherein the first and second electrode groups are arranged on left/right surfaces of the flow channel with respect to a flow direction.

7. The apparatus according to claim 1, wherein the first and second electrode groups are implemented such that a plurality of electrode groups is additionally arranged in series.

8. The apparatus according to claim 1, wherein the first and second electrode groups are implemented such that a plurality of electrodes is additionally arranged in parallel.

9. The apparatus according to claim 1, wherein the electrode pairs of the first and second electrode groups are implemented using a single common electrode.

10. A method of detecting motion characteristics of particles in a flow channel, using an apparatus for detecting motion characteristics of claim 1, the method comprising:
a first step of directly applying voltage to first and second electrode groups, thus generating respective electric fields in the flow channel;
a second step of moving the particles placed in the flow channel, thus causing the particles to vary electrical pulses while the particles pass through electrical fields generated in the first and second electrode groups; and,
a third step of detecting at least one of the motion characteristics of particles from the group including: location of the particles in a transverse direction of the flow channel, a speed of the particles in a longitudinal direction of the flow channel, and a traveling direction of the particles on the basis of variation in electrical pulses measured in the first and second electrode groups.

11. The method according to claim 10, wherein, at the third step, the location of the particles in the transverse direction of the flow channel is detected on a basis of a ratio of durations of electrical pulses measured in the first and second electrode groups.

12. The method according to claim 10, wherein, at the third step, the traveling direction of the particles in the flow channel in the longitudinal direction of the flow channel is detected on a basis of a sequence of generation of the electrical pulses respectively measured in the first and second electrode groups.

13. The method according to claim 10, wherein, at the third step, the speed of the particles in the flow channel in the longitudinal direction of the flow channel is detected on a basis of a sum of durations of the electrical pulses respectively measured in the first and second electrode groups, and a sum of a distance $l_1(P)$ between the first group electrodes in the longitudinal direction and the distance $l_2(P)$ between the second group electrodes in the longitudinal direction.

14. An apparatus for detecting motion characteristics of particles in a flow channel through which a fluid containing the particles flows, comprising:
a pair of drive electrodes arranged to be spaced apart from each other in the flow channel, and adapted to apply a voltage;
first and second electrode groups, each electrode group comprising a pair of sensing electrodes arranged to be spaced apart from each other between the drive electrodes and adapted to measure impedance between each pair of sensing electrodes; and,
an operation control unit for measuring variation in electrical pulses generated in the first and second electrode groups, as the particles pass through the first and second electrode groups, thus detecting the motion characteristics of particles,
wherein the first electrode group and the second electrode group are sequentially arranged in a longitudinal direction X of the flow channel with the pair of electrodes of each group being positioned on the same surface plane of the flow channel, one electrode of the first electrode group is inclined at a first angle to the other electrode so that a distance $l_1(P)$ by which the electrodes of the first electrode group are spaced apart from each other in the longitudinal direction is increased in a specific transverse direction Y of the flow channel, while one electrode of the second group is inclined at a second angle to the other electrode so that a distance $l_2(P)$ by which the electrodes of the second group are spaced apart from each other in the longitudinal direction is decreased in the specific transverse direction of the flow channel.

15. The apparatus according to claim 14, wherein the first angle is identical to the second angle.

16. The apparatus according to claim 14, wherein the first and second angles are selected such that one of the pair of electrodes of each of the first and second electrode groups is arranged to be inclined at a certain angle to the transverse direction, and a remaining one thereof is arranged in the transverse direction of the flow channel.

17. The apparatus according to claim 14, wherein the electrodes are bar-type electrodes, bent electrodes or stepped electrodes.

18. The apparatus according to claim 14, wherein the first and second electrode groups are arranged on upper/lower surfaces of the flow channel with respect to the flow direction.

19. The apparatus according to claim 14, wherein the first and second electrode groups are arranged on left/right surfaces of the flow channel with respect to a flow direction.

20. The apparatus according to claim 14, wherein the first and second electrode groups are implemented such that a plurality of electrode groups is additionally arranged in series.

21. The apparatus according to claim 14, wherein the first and second electrode groups are implemented such that a plurality of electrodes is additionally arranged in parallel.

22. The apparatus according to claim 14, wherein the electrode pairs of the first and second electrode groups are implemented by using a single electrode as a common electrode.

23. A method of detecting motion characteristics of particles in a flow channel, using an apparatus for detecting motion characteristics of claim 14, the method comprising:
a first step of applying voltage to the pair of drive electrodes, thus generating electric fields in the flow channel;
a second step of moving the particles in the flow channel, thus causing the particles to vary electrical pulses while the particles pass through the electrical fields generated in first and second electrode groups, each comprising a pair of sensing electrodes arranged to be spaced apart from each other between the drive electrodes forming the pair; and,
a third step of detecting at least one of the motion characteristics of particles from the group including: location of the particles in a transverse direction of the flow channel, a speed of the particles in a longitudinal direction of the flow channel, and a traveling direction of the particles on the basis of variation in electrical pulses measured in the first and second electrode groups.

24. The method according to claim 23, wherein at the third step, the location of the particles in the transverse direction of the flow channel is detected on a basis of a ratio of durations of electrical pulses measured in the first and second electrode groups.

25. The method according to claim 23, wherein, at the third step, the traveling direction of the particles in the flow channel in the longitudinal direction of the flow channel is detected on a basis of a sequence of generation of the electrical pulses respectively measured in the first and second electrode groups.

26. The method according to claim 23, wherein, at the third step, the speed of the particles in the flow channel in the longitudinal direction of the flow channel is obtained by using a sum of durations of the electrical pulses respectively measured in the first and second electrode groups, and a sum of a distance $l_1(P)$ between the first group electrodes in the longitudinal direction and the distance $l_2(P)$ between the second group electrodes in the longitudinal direction.

* * * * *